(12) United States Patent
Wang et al.

(10) Patent No.: US 12,150,972 B1
(45) Date of Patent: Nov. 26, 2024

(54) EGG WHITE PROTEIN ANTI-INFLAMMATORY PEPTIDE AND APPLICATION THEREOF

(71) Applicants: Hangzhou BIBAU Biotechnology Co., Ltd., Zhejiang (CN); Beijing Forestry University, Beijing (CN)

(72) Inventors: Aqin Wang, Zhejiang (CN); Difeng Ren, Zhejiang (CN); Jun Yu, Zhejiang (CN); Yaxin Liang, Zhejiang (CN)

(73) Assignees: Hangzhou BIBAU Biotechnology Co., Ltd., Zhejiang (CN); Beijing Forestry University, Beijing (CN)

( * ) Notice: Subject to any disclaimer, the term of this patent is extended or adjusted under 35 U.S.C. 154(b) by 0 days.

(21) Appl. No.: 18/600,947

(22) Filed: Mar. 11, 2024

(30) Foreign Application Priority Data

Jul. 4, 2023 (CN) .......................... 202310811456.5

(51) Int. Cl.
*A61K 38/06* (2006.01)
*A61P 29/00* (2006.01)

(52) U.S. Cl.
CPC .............. *A61K 38/06* (2013.01); *A61P 29/00* (2018.01)

(58) Field of Classification Search
None
See application file for complete search history.

(56) References Cited

U.S. PATENT DOCUMENTS

2013/0330335 A1* 12/2013 Bremel .................. G16B 20/00
435/69.6

OTHER PUBLICATIONS

Joseph Provost, The Maillard Reaction, Chapter 14 of Food Aroma Evolution, 2019, pp. 281-291 (Year: 2019).*

* cited by examiner

*Primary Examiner* — Melissa L Fisher
*Assistant Examiner* — Joseph Fischer
(74) *Attorney, Agent, or Firm* — Cooper Legal Group, LLC (57) ABSTRACT

The present application relates to the technical field of active peptides, and particularly relates to an egg white protein anti-inflammatory active peptide and preparation and application of Maillard reaction product thereof. The anti-inflammatory peptide is FGPH, and when the concentration of the anti-inflammatory peptide is 500 µg/mL, the inhibition ratios of the anti-inflammatory peptide to an inflammatory mediator (NO) and inflammatory factors (TNF-alpha, IL-6 and IL-1 beta) of RAW264.7 induced by LPS are 64.41±0.47%, 28.07±2.10%, 41.72±1.83% and 52.43±2.29%, respectively.

3 Claims, 8 Drawing Sheets
(4 of 8 Drawing Sheet(s) Filed in Color)
Specification includes a Sequence Listing.

EGG WHITE PROTEIN ANTI-INFLAMMATORY PEPTIDE AND APPLICATION THEREOF

CROSS-REFERENCE TO RELATED APPLICATION

This application is based on and claims the priority and benefit of Chinese patent application serial no. 202310811456.5, filed on Jul. 4, 2023. The entirety of Chinese patent application serial no. 202310811456.5 is hereby incorporated by reference herein and made a part of this specification.

FIELD OF THE INVENTION

The present application relates to the technical field of active peptides, and particularly relates to an egg white protein anti-inflammatory active peptide and preparation and application of a Maillard reaction product thereof.

REFERENCE TO AN ELECTRONIC SEQUENCE LISTING

The contents of the electronic sequence listing (SequenceListing.xml; Size: 8,771 bytes; and Date of Creation: Mar. 11, 2024) is herein incorporated by reference.

DESCRIPTION OF RELATED ART

The bioactive peptides are derived from proteins and refer to the biologically active fragments therein. The bioactive peptides have unique biological activities beyond basic nutritional needs and have attracted more and more attention due to their contribution to human health. Because peptides are complex structures hidden in the parent protein, it is difficult to effectively exert their biological activity. After biochemical reactions such as external protease hydrolysis and fermentation, or gastrointestinal digestion, a variety of physiological functions can be produced and a positive impact on human health can be achieved.

In recent years, many studies have been focused on the identification of novel hen egg white protein peptide, and the publication of the chicken genome has greatly improved the ability to identify proteins and peptides in complex samples. Studies have shown that different types of bioactive peptides can be obtained from hen egg white protein after enzymatic hydrolysis by specific proteases.

The Maillard reaction refers to the chemical reaction between amino compounds such as proteins, peptides, and amino acids, and carbonyl compounds such as reducing sugars, aldehydes, and ketones. The controlled Maillard reaction can produce products that have desirable sensory properties including color and flavor, and can also influence the biological activity.

At present, the bioactive peptides have been used in prevention and treatment. As a country with a large hen egg production, China ranks first in the production and consumption of hen egg in the world. Hen egg white has rich proteins and contains a large amount of bioactive substances, and has the physiological functions such as preventing and treating diseases and immune regulation. Currently, there is little in-depth development and utilization of hen egg white, resulting in a large amount of high-quality protein resources being wasted, and there lacks deep processing and utilization of hen egg white protein anti-inflammatory active peptides. Therefore, using hen egg white protein as raw material to develop high-quality hen egg white polypeptide products has good prospects and significance.

BRIEF SUMMARY OF THE INVENTION

Hen egg white has rich proteins and is an important source of bioactive peptides. The activity and flavor of the proteins/peptides after Maillard reaction can be further improved. Therefore, the present application utilizes hen egg white proteolysis to prepare polypeptides, and explores the changes in activity and flavor of the polypeptides after Maillard reaction.

One of the technical solutions provided by the present application is an anti-inflammatory active peptide from hen egg white. The amino acid sequence of the anti-inflammatory active peptide is: Phe-Gly-Pro-His (SEQ ID NO: 1), hereinafter referred to as FGPH;

The anti-inflammatory peptide FGPH can be obtained by enzymolysis screening of hen egg white, or can be obtained by artificial synthesis.

The second technical solution provided by the present application is the use of the above-mentioned active peptide FGPH in anti-inflammatory responses, especially in the preparation of anti-inflammatory drugs, food or other products.

The third technical solution provided by the present application is FGPH-MRPs, the Maillard reaction product of FGPH.

Further, the preparation method for FGPH-MRPs includes the following steps: weighing and preparing FGPH into an aqueous solution, adding a dextran according to a peptide to dextran mass ratio of 1.5:1, mixing thoroughly, reacting at 80° C. and pH 9.0 for 10 hours, and cooling to room temperature after the reacting is completed, to obtain the Maillard product of FGPH, FGPH-MRPs.

The fourth technical solution provided by the present application is the use of the Maillard reaction product of FGPH, i.e., FGPH-MRPs described in the third technical solution, especially in the anti-inflammatory response, especially in a preparation of anti-inflammatory drugs, food or other products.

Beneficial Effects

In the present application, an anti-inflammatory polypeptide is prepared from hen egg white by enzymatic hydrolysis, and a polypeptide FGPH with high anti-inflammatory activity is obtained after a series of separation, purification, identification and synthesis. The anti-inflammatory activity of FGPH was verified after artificially synthesis. It was found that at a concentration of 500 μg/mL, the inhibition ratios of FGPH to the inflammatory mediator (NO) and inflammatory factors (TNF-α, IL-6, IL-1β) of RAW264.7 induced by LPS (lipopolysaccharide) are 64.41±0.47%, 28.07±2.10%, 41.72±1.83%, and 52.43±2.29%, respectively.

The effect of the Maillard reaction on the activity and flavor of the anti-inflammatory active peptide FGPH is further explored. Fourier transform infrared spectroscopy and scanning electron microscopy are used to explore the Maillard product FGPH-MRPs, and it is found that its structure and morphology have changed compared with before the reaction. The changes in activity before and after the Maillard reaction were measured, and it is found that, in the RAW264.7 cells induced by LPS, the inhibition ratio of NO production amount increased from 64.41±0.47% to 68.16±0.48%, and the $EC_{50}$ values of DPPH, ABTS, and hydroxyl radical scavenging rates decreased from 4.96±0.05 mg/mL to 4.07±0.03 mg/mL, from 0.81±0.01 mg to 0.61±0.01 mg/mL, and from 2.01±0.03 mg/mL to 1.56±0.02 mg/mL, respectively. The taste of FGPH determined by sensory evaluation and electronic tongue evaluation was improved, and the characteristic odor response value determined by electronic nose evaluation was significantly improved. It is indicated that the NO inhibition ratio, antioxidant activity and flavor of FGPH are improved through the Maillard reaction.

BRIEF DESCRIPTION OF DRAWINGS

The patent or application file contains at least one drawing executed in color. Copies of this patent or patent application publication with color drawing(s) will be provided by the Office upon request and payment of the necessary fee.

DETAILED DESCRIPTION

In order to make the purpose, technical solutions and advantages of the present application more clear, the present application will be further described in detail below in combination with specific examples. It should be understood that the specific examples described herein are only used to explain the present application and are not intended to limit the present application.

The anti-inflammatory peptide FGPH of the present application can be obtained by enzymolysis screening of hen egg white, or can be obtained by artificial synthesis.

Some of the test methods adopted in the present application are as follows:

1. Determination of Anti-Inflammatory Activity 1.1 RAW264.7 Cell Culture

The DMEM culture medium containing 10% fetal bovine serum was prepared. The mouse macrophage RAW264.7 was activated and quickly added to the culture medium. The cell morphology was observed under a microscope and the culture medium was transferred to an incubator for culture. The temperature of the incubator was set to 37° C., and the CO2 concentration was set to 5%. The cell morphology was observed and the cell was passaged every 24 hours. The cells were digested by adding 0.25% trypsin (containing 0.01% EDTA), washed and centrifuged with DMEM medium, and washed and centrifuged with PBS. The cells were inoculated into culture dishes for subsequent experimental operations.

1.2 Effect on RAW264.7 Cell Viability

The cell viability of RAW264.7 cells was determined by MTT method. RAW264.7 cells in the logarithmic growth phase were seeded in a 96-well plate at 100 μL/well with a density of 4×104/well. The outermost layer of the 96-well plate was sealed by PBS solution, and the 96-well plate was transferred to an incubator for culturing for 12 to 24 hours. The incubator temperature was 37° C. and the CO2 concentration was 5%. After the cells adhered to the wall, the waste supernatant was extracted from the 96-well plate. A blank group (added with 100 μL of culture medium), an LPS group (added with 100 μL of LPS with a final mass concentration of 1 μg/mL), and a sample group (added with 100 μL of peptides with different or the same mass concentration and added with LPS with a final mass concentration of 1 μg/mL after 2 hours of reaction) were set, and each group was performed in triplicate. After culturing for 24 hours, 20 μL of MTT solution with a concentration of 5 mg/mL was added into each well. After continuing to culture in the incubator for 4 hours, 100 μL of dimethyl sulfoxide (DMSO) was added and shaken gently for 10 min. The absorbance value at 570 nm was measured with a microplate reader, and the cell viability (%) was calculated according to the formula (1).

$$V(\%) = \frac{A_2}{A_1} \times 100 \quad (1)$$

In the formula (1), V refers to the cell viability (%), $A_1$ is the absorbance value of the blank group at 570 nm, and $A_2$ is the absorbance value of the sample group at 570 nm.

1.3 Effect on NO Production Amount in RAW264.7 Cells

The NO production amount in the cell was measured by Griess method. The grouping, treatment and culture methods were the same as 1.2. After 24 hours of culture, the supernatant was collected and the NO production amount was measured using a NO detection kit. 50 μL of cell supernatant, 50 μL of Griess I reagent, and 50 μL of Griess II reagent were mixed, and stood for 5 minutes, and then the absorbance value at 540 nm was measured. According to the instructions of the NO kit, the NO production amount in each sample was calculated, and the inhibition ratio of NO production amount is calculated by formula (2).

$$B(\%) = \frac{B_1 - B_2}{B_1 - B_0} \times 100 \quad (2)$$

In the formula, B refers to the NO inhibition ratio (%), $B_0$ is the NO production amount of the blank group, $B_1$ is the NO production amount of the LPS group, and $B_2$ is the NO production amount of the sample group.

1.4 Determination of Cytokines TNF-α, IL-6, and IL-1β

RAW264.7 cells in the logarithmic growth phase were seeded into a 96-well plate at 100 L/well, with a density of 4×10⁴/well, and 3 replicates were designed for each well. A blank group (added with 100 μL of culture medium), an LPS group (added with 100 μL of LPS with a final mass concentration of 1 µg/mL), and a sample group (added with 100 µL of peptides of different concentrations, and with a final mass concentration of 1 µg/mL LPS after 2 hours of reaction) were set. The three groups were cultured in the incubator for 24 hours, and the supernatants were collected. According to the instructions of the ELISA kit, the absorbance value at 450 nm was measured and the secretion amounts of inflammatory factors TNF-α, IL-6 and IL-1β were calculated. The inhibition ratios of the three inflammatory factors were calculated by formula (3).

$$C(\%) = \frac{C_1 - C_2}{C_1 - C_0} \times 100 \quad (3)$$

In the formula, C refers to the inhibition ratio (%) of inflammatory factors, $C_0$ is the secretion amount of inflammatory factors in the blank group, $C_1$ is the secretion amount of inflammatory factors in the LPS group, and $C_2$ is the secretion amount of inflammatory factors in the sample group.

2. Determination of Antioxidant Activity 2.1 1,1-diphenyl-2-picrylhydrazyl (DPPH) Free Radical Scavenging Rate The polypeptide antioxidant properties DPPH was determined according to GB/T39100-2020. Preparation of DPPH solution: 5 mg of DPPH was fully dissolved in an appropriate amount of absolute ethanol by using ultrasonic in the dark, and the volume was adjusted to 100 mL. DPPH solution with a concentration of 50 µg/mL was prepared on site. Preparation of peptide solution: 10 mg of the peptide was completely dissolved in an appropriate amount of distilled water, and the volume was adjusted to 1 mL, to prepare a peptide solution with a concentration of 10 mg/mL, and the peptide solution was diluted according to a certain ratio to obtain peptide solutions of different concentrations. The regents were added into three test tubes numbered 1, 2, and 3, according to Table 1, and the absorbance value at 517 nm was measured. The DPPH free radical scavenging rate was calculated by formula (4). Taking the natural logarithm value of the peptide solution concentration as the abscissa and the DPPH free radical scavenging rate as the ordinate, a linear equation between the natural logarithm value of the peptide concentration and the scavenging rate was obtained, and the semi-maximum effect concentration $EC_{50}$ of the DPPH free radical scavenging rate was calculated.

$$P1(\%) = \left(1 - \frac{A_s - A_c}{A_b}\right) \times 100 \quad (4)$$

In the formula, P1 refers to the DPPH free radical scavenging rate (%), As is the absorbance value at 517 nm after the DPPH solution is mixed with the peptide solution, Ac is the absorbance value at 517 nm after the peptide solution is mixed with the ethanol solution, and $A_b$ is the absorbance value at 517 nm after the DPPH solution is mixed with the sample reagent solution.

TABLE 1 the reagent addition amount of the DPPH free radical scavenging experiment

| Sample | Test tube 1 ($A_s$) | Test tube 2 ($A_c$) | Test tube 3 ($A_b$) |
|---|---|---|---|
| DPPH solution (mL) | 3.0 | — | 3.0 |
| Peptide solution (mL) | 1.0 | 1.0 | — |
| Sample solvent solution (mL) | — | — | 1.0 |
| Ethanol solution (mL) | — | 3 | — |

2.2 2,2-azino-bis(3-ethyl-benzothiazole-6-sulfonic acid) diammonium salt (ABTS) Free Radical Scavenging Rate The polypeptide antioxidant assay ABTS was performed according to GB/T39100-2020. Preparation of ABTS solution: 200 mg of ABTS reagent and 34.4 mg of potassium persulfate were added and fully dissolved in 50 mL of distilled water, shaken evenly, and stored in the dark at room temperature for 24 hours. The ABTS test solution was prepared by being diluted with 95% ethanol to make the absorbance value at 734 nm was 0.70±0.02. The solution was prepared when it will be used. 10 mg of the polypeptide was completely dissolved in an appropriate amount of distilled water, and the volume was adjusted to 1 mL, to prepare a polypeptide solution with a concentration of 10 mg/mL. 95% ethanol solution was used to dilute the solution to different multiples to obtain polypeptide solutions of different concentrations. The reagents were added to two test tubes numbered 1 and 2 according to Table 2, and the absorbance value at 734 nm was measured. The ABTS free radical scavenging rate is calculated by formula (5). The calculation method of $EC_{50}$ was the same as 2.1.

$$P2(\%) = \left(\frac{A_b - A_s}{A_b}\right) \times 100 \quad (5)$$

In the formula, P2 refers to the ABTS free radical scavenging rate (%); $A_b$ is the absorbance value at 734 nm after the ABTS solution was mixed with the sample reagent solution; As is the absorbance value at 734 nm after the ABTS solution was mixed with the peptide solution.

TABLE 2 the reagent addition amount of the ABTS free radical scavenging experiment

| Sample | Test tube 1 ($A_s$) | Test tube 2 ($A_b$) |
|---|---|---|
| ABTS solution (mL) | 3.6 | 3.6 |
| Peptide solution (mL) | 0.4 | — |
| Sample solvent solution (mL) | — | 0.4 |

2.3 Hydroxyl Radical Scavenging Rate

The hydroxyl radical scavenging rate was determined according to the method of Chen et al. Preparation of the reaction solution: appropriate amounts of ferrous sulfate, hydrogen peroxide and salicylic acid were fully dissolved in the distilled water, to prepare 9 mmol/L ferrous sulfate solution, 8.8 mmol/L hydrogen peroxide solution and 9 mmol/L salicylic acid solution. Preparation of the peptide solution: 10 mg of the peptide was completely dissolved in an appropriate amount of distilled water, and the volume was adjusted to 1 mL, to prepare a peptide solution with a concentration of 10 mg/mL, and the peptide solution was diluted according to a certain ratio to obtain peptide solutions of different concentrations. 1 mL of polypeptide solutions of different concentrations was added in a test tube, mixed evenly with 1 mL of ferrous sulfate, and 1 mL of salicylic acid and reacted for 10 minutes. Then 1 mL of hydrogen peroxide solution was added in the test tube and placed at 37° C. for 30 minutes for reacting. The absorbance value at 510 nm was measured. 1 mL of distilled water was taken instead of the peptide solution, the same operation as described above was performed, and its absorbance value at 510 nm was measured. 1 mL of distilled water was taken instead of the hydrogen peroxide solution, the same operation as described above was performed, and its absorbance value at 510 nm was measured. The hydroxyl radical scavenging rate was calculated by formula (6). The calculation method of $EC_{50}$ was the same as 2.1.

$$P3(\%) = \left[1 - \left(\frac{A_i - A_j}{A_0}\right)\right] \times 100 \quad (6)$$

In the formula, P3 refers to the hydroxyl radical scavenging rate (%); $A_i$ is the absorbance value of the peptide solution at 510 nm; $A_j$ is the absorbance value at 510 nm when the hydrogen peroxide solution was replaced by the distilled water; $A_0$ is the absorbance value at 510 nm when the peptide solution was replaced by the distilled water.

3. LC-MS/MS Separation and Identification

The amino acid sequence and molecular weight of the polypeptide components were determined using LC-MS/MS. Before the sample was measured, the sample was first subjected to reductive alkylation and desalting treatment. The capillary liquid chromatography pre-column used was a 300 μm×5 mm Acclaim PepMap RPLC C18 analytical column (5 μm, 100 Å), and the analytical column was a 150 μm×150 mm Acclaim PepMap RPLC C18 analytical column (1.9 m, 100 Å). Mobile phase A was 0.1% (v/v) formic acid solution and 2% (v/v) acetonitrile solution, and mobile phase B was 0.1% (v/v) formic acid solution and 80% (v/v) acetonitrile solution. The flow rate is 600 mL/min, and the analysis time of each component was 60 min.

MS and MS/MS parameters were as follows:
(1) MS parameters: the resolution was 70000; the maximum injection time was 40 ms; the scanning range was 300-1400 m/z.
(2) MS/MS parameters: the resolution was 175000; the maximum injection time was 60 ms; the scanning range was 300-1400 m/z; Top N=20; NCE/steeped NCE=27.
the original MS/MS file was analyzed according to Mascot software of the sample type and searched and compared with the Uniprot database (https://www.uniprot.org/) *Gallus gallus* (Chicken) to determine the amino acid sequence of the peptide.

The present application will be further explained below with reference to the specific examples.

Example 1 Enzymatic Hydrolysis of the Hen Egg White Protein Peptides

1. Preheating to Prepare Peptides

The hen egg white protein was dissolved in the distilled water with a substrate concentration of 4% (w/v), placed in a water bath at 90° C. to be pre-cooked for 20 minutes, then cooled to 45° C. after pre-cooking. The pH value of the protein solution was adjusted to 7.5, the temperature of the protein solution was adjusted to 45° C. 3000 U/g of complex protease (C8800, Solarbio) was added according to the mass of the substrate, and the enzymatic hydrolysis was performed for 1.5 hours; the pH value was adjusted to 10.0, and the temperature was adjusted to 40° C. 3000 U/g of alkaline protease was added according to the mass of the substrate, the enzymatic hydrolysis was performed for 1.5 h; the pH value was adjusted to 7.5, and the temperature was adjusted to 50° C. 3000 U/g of flavor protease was added according to the mass of the substrate, the enzymatic hydrolysis was performed for 1.5 h, immediately boiled for 10 minutes to kill the enzyme after the enzymatic hydrolysis, and then the enzymatic solution was centrifuged at 6000 r/min for 20 minutes to remove residual proteins and obtain the supernatant, the pH value was adjusted to 7.0 and the freeze-drying was performed for subsequent use.

The biuret method was used to determine the yield of the polypeptide, and the yield was 42.08±0.48%.

2. Ultrafiltration Separation of Polypeptides

The enzymatic hydrolyzate of the hen egg white protein was centrifuged at 6000 r/min for 20 minutes to obtain the supernatant. First, the enzymatic hydrolyzate was filtered through a 0.45 m filter membrane, and the filtrate was collected for the next step. The filtrate was separated using ultrafiltration membranes of 10 kDa, 5 kDa, and 3 kDa. Polypeptides of different molecular weights (>10 kDa, 5-10 kDa, 3-5 kDa, and <3 kDa) were collected. The four polypeptide solutions of different molecular weights were vacuum freeze-dried and stored at −80° C.

Figure 1:
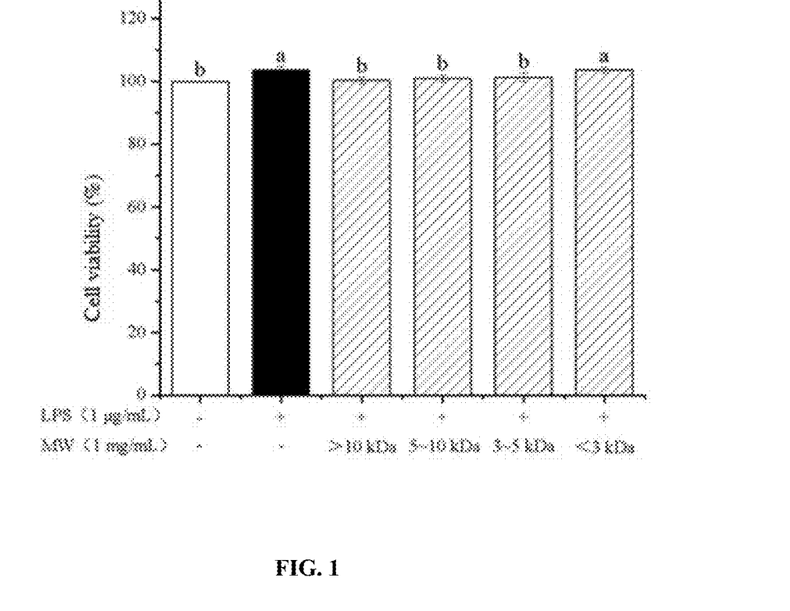
FIG. 1 illustrates the effects of polypeptides of different molecular weights (greater than 10 kDa, 5-10 kDa, 3-5 kDa, and less than 3 kDa) on the cell viability.

3. Determination of Anti-Inflammatory Activity 3.1 Effect on RAW264.7 Cell Viability 1 mg/mL was set as the final concentration of the enzymatic hydrolyzate with molecular weights >10 kDa, 5-10 kDa, 3-5 kDa, and <3 kDa, and the cell viability of the four samples were measured. As shown in FIG. 1, after the four samples were added, the viability of LPS-induced RAW264.7 cells was all above 100%, and there was no toxic effect. Among them, the cells treated with enzymatic hydrolyzate with molecular weight <3 kDa had the highest cell viability, reaching 103.62±0.84%.

3.2 Effect of Polypeptides with Molecular Weight <3 kDa on NO Production Amount

Figure 2:
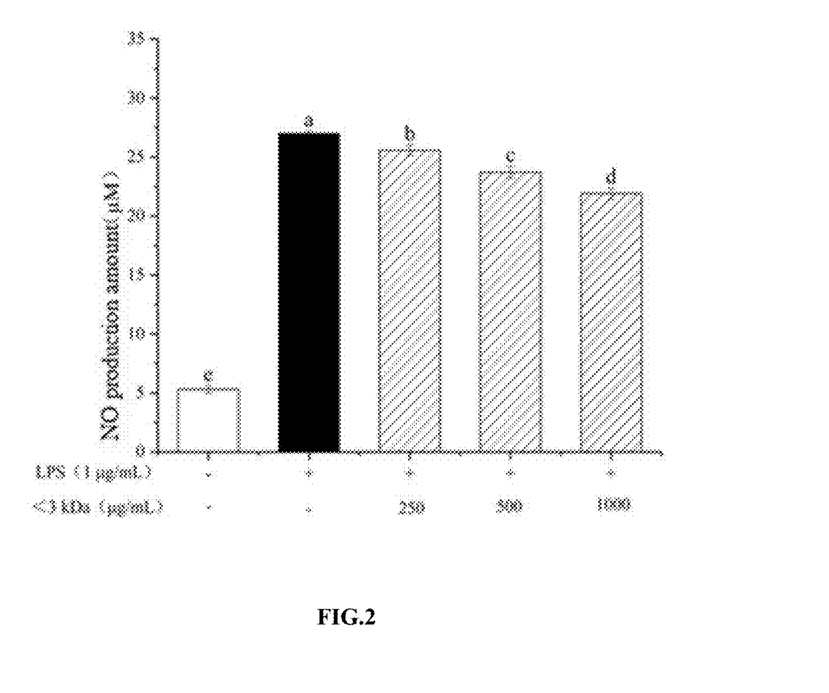
FIG. 2 illustrates the effect of polypeptide with a molecular weight of less than 3 kDa on NO production amount.

Effects of polypeptide components with molecular weight <3 kDa in the concentration range of 250 to 1000 μg/mL on NO production amount in RAW264.7 macrophages induced by LPS. As shown in FIG. 2, after being induced by LPS at a concentration of 1 μg/mL, the NO production amount of RAW264.7 cells increased significantly (P<0.05), which was approximately 5.08 times that of the blank group, indicating that the RAW264.7 macrophage inflammation model induced by LPS was successfully established. When the concentration of the peptide component with a molecular weight <3 kDa was 1000 g/mL, the NO production amount was the lowest, which was 21.57±0.47 μM.

3.3 Antioxidant Activity of Polypeptides with Molecular Weight <3 kDa

The $EC_{50}$ value of the antioxidant capacity of the polypeptide component with a molecular weight of <3 kDa was shown in Table 3. The polypeptide component with a molecular weight of <3 kDa has the ability to scavenge three free radicals: DPPH, ABTS and hydroxyl radicals, so it has certain antioxidant activity. Free radicals and inflammatory reactions are interrelated.

Inflammation involves the excessive production and release of reactive oxygen species, such as hydroxyl radicals, superoxide anion free radicals, singlet oxygen, etc. Polypeptides with good antioxidant activity usually have better anti-inflammatory potential. It is necessary to explore the antioxidant and anti-inflammatory activities of bioactive peptides at the same time.

TABLE 3

Antioxidant capacity of polypeptide components with molecular weight <3 kDa

| Antioxidant activity | $EC_{50}$ value (mg/mL) |
|---|---|
| Scavenging DPPH free radical | 1.97 ± 0.01 |
| Scavenging ABTS free radical | 1.17 ± 0.01 |
| Scavenging hydroxyl radical | 2.84 ± 0.01 |

Example 2 Separation and Identification of Hen Egg White Protein Peptide

Figure 3:
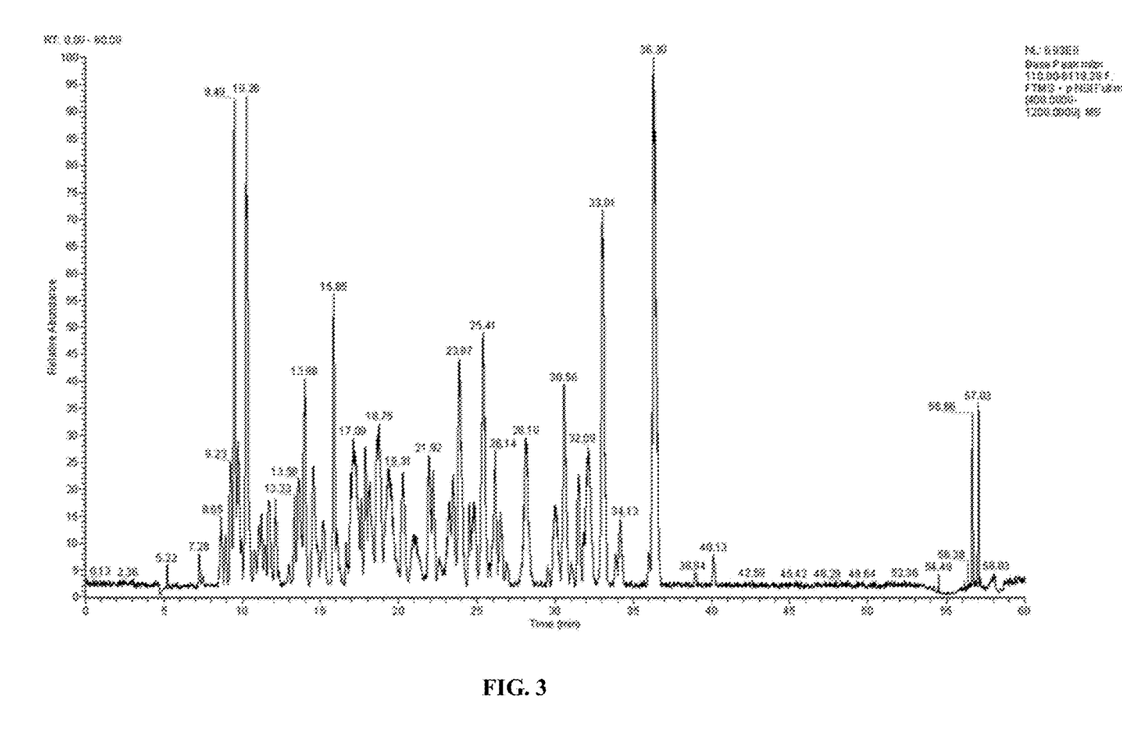
FIG. 3 is the total ion chromatogram of polypeptide components with a molecular weight of less than 3 kDa.

LC-MS/MS liquid mass analysis was performed on peptide components with molecular weight <3 kDa. The total ion chromatogram was shown in FIG. 3. Through LC-MS/MS analysis and database search and comparison, a total of 790 peptide sequences were obtained.

2. Virtual Screening and Molecular Docking 2.1 Virtual Screening

A 2D structure diagram of the peptide from the peptide sequence obtained by LC/MS-MS was drawn, and then a 3D structure diagram of the peptide was drawn and was set to be a structure with the smallest energy (pdbqt format). The x-ray crystal structure (PDB format) of inducible NO synthase (iNOS, PDB ID: 3e6t) was downloaded from the RCSB Protein Data Bank database, and Autodock tools1.5.6 software was used to perform the operations of removing water molecules, hydrogenating and calculating charge to the receptor iNOS. All peptide fragments and receptor proteins were docked separately through PyRx 0.8 software. Generally, the docking energy was less than 0. The smaller the value, the tighter the docking and the higher the anti-inflammatory potential. Therefore, the peptide fragments were sorted according to the absolute value of the docking energy, the top-ranked peptides ranked using Peptide Ranker (http://distilldeep.ucd.ie/PeptideRanker/) was used to predict the possible biological activity value.

Inducible nitric oxide synthase (iNOS) is a nervous system enzyme closely related to inflammatory response. When stimulated by various inflammatory conditions, a large amount of iNOS expression was induced by LPS or cytokines, and then NO was produced continuously, which may lead to tissue damage at the inflammation site. Controlling iNOS is one of the important strategies to control inflammatory responses in various pathological conditions, and iNOS has become a key target in the treatment of inflammatory diseases. PyRx software can simulate docking of receptors and different ligands in batches, and judge the strength of their interaction through the docking energy to achieve virtual screening effects. The docking energy score indicates the binding potential of the receptor and the ligand. Generally speaking, a lower score represents a stronger binding ability between the two. As shown in Table 4, the peptides obtained by LC-MS/MS were simulated and scored and the docking energy was ranked. The docking energy of the top 6 peptides was ≤−8.5 kcal mol$^{-1}$, indicating that the binding ability to iNOS was relatively strong. The six peptides were compared with the BIOPEP-UWM database. WINPIGT and WNIP were synthesized and verified as antioxidant peptides, and RADHPFL was synthesized and verified as an angiotensin-converting enzyme inhibitory peptide. The six peptides are all bioactive peptides derived from hen egg white. In particular, the peptide fragment phenylalanine-glycine-proline-histidine (FGPH) is not consistent with any one of the known bioactive peptide sequences in the BIOPEP-UWM database. And among the unstudied peptides, the docking energy is the lowest at −9.3 kcal mol$^{-1}$, indicating that FGPH may have a strong inhibitory effect on iNOS and is a potential new anti-inflammatory active peptide.

Table 4

Comparison results between virtual screening and BIOPEP-UWM peptide database

| Peptide fragment sequence | Docking energy (kcal mol$^{-1}$) | BIOPEP-UWM peptide fragment database |
|---|---|---|
| WNIPIGT (SEQ ID NO: 2) | −9.4 | AGWNIPIGT (SEQ ID NO: 3) (antioxidant) |
| FGPH (SEQ ID NO: 1) | −9.3 | No |
| WNIP (SEQ ID NO: 4) | −9.0 | AGWNIPIGT (SEQ ID NO: 5) (antioxidant) |
| RADHPFL (SEQ ID NO: 6) | −8.9 | RADHPFL (ACE inhibitory) |
| FPF | −8.8 | FPFEVFGK (SEQ ID NO: 7) (ACE inhibitory) |
| FGRCVSP (SEQ ID NO: 8) | −8.5 | FFGRCVSP (SEQ ID NO: 9) (ACE inhibitory) |

The possible biological activities of the six peptides were ranked by Peptide Ranker, and the toxicity and physical and chemical properties of the peptides were evaluated using the ToxinPred program. The results are shown in Table 5. None of the six peptides were predicted to be toxic. The biological activity score of FGPH in Peptide Ranker is 0.93, indicating that FGPH may have good biological activity.

TABLE 5

Bioactivity scores and prediction of physical and chemical properties of peptides

| Peptide sequence | Scores | Toxicity | Hydrophobicity | Hydrophilia | Steric hindrance | Amphipathy |
|---|---|---|---|---|---|---|
| WNIPIGT | 0.71 | No | 0.16 | −1.03 | 0.60 | 0.00 |
| FGPH | 0.93 | No | 0.07 | −0.75 | 0.43 | 0.36 |
| WNIP | 0.86 | No | 0.10 | −1.25 | 0.58 | 0.00 |
| RADHPFL | 0.84 | No | −0.22 | 0.10 | 0.51 | 0.56 |
| FPF | 0.99 | No | 0.38 | −1.67 | 0.59 | 0.00 |
| FAGHP | 0.82 | No | 0.11 | −0.70 | 0.29 | 0.35 |

Figure 4:
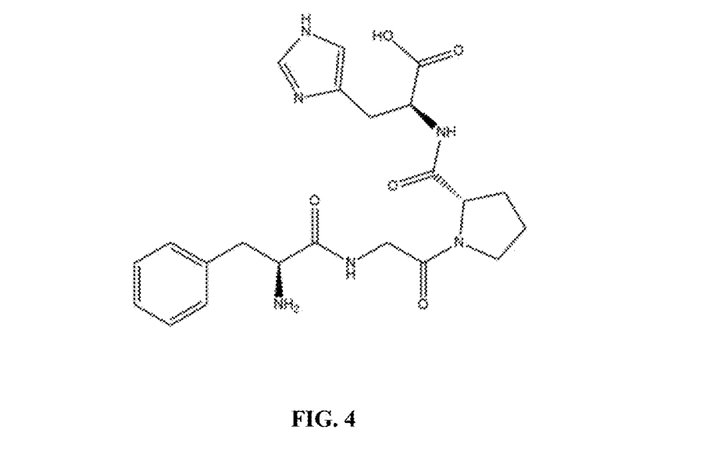
FIG. 4 illustrates the chemical structure of FGPH.

The chemical structure of the potential anti-inflammatory active peptide Phe-Gly-Pro-His (FGPH) was shown in FIG. 4.

2.2 Molecular Docking

The docking software was Autodock Vina. The peptides in pdbqt format were used as ligands, and the iNOS in PDB format downloaded from RCSB Protein Data Bank was used as the receptor, and the two are semi-flexibly docked. Discovery studio 2.5 software was used to visually analyze the interaction between single small molecules and ligands.

The anti-inflammatory mechanism of FGPH was studied through molecular docking, and 10 FGPH was docked with the receptor protein iNOS. FGPH was docked in the cavity of iNOS, and hydrogen bonds, carbon-hydrogen bonds, and cation-πc interactions are the main forces between the peptide and iNOS. The docking results indicate that the absolute value of the docking energy of FGPH and iNOS is 9.3 kcal mol-1. FGPH is bound tightly to receptor proteins.

Figure 5:
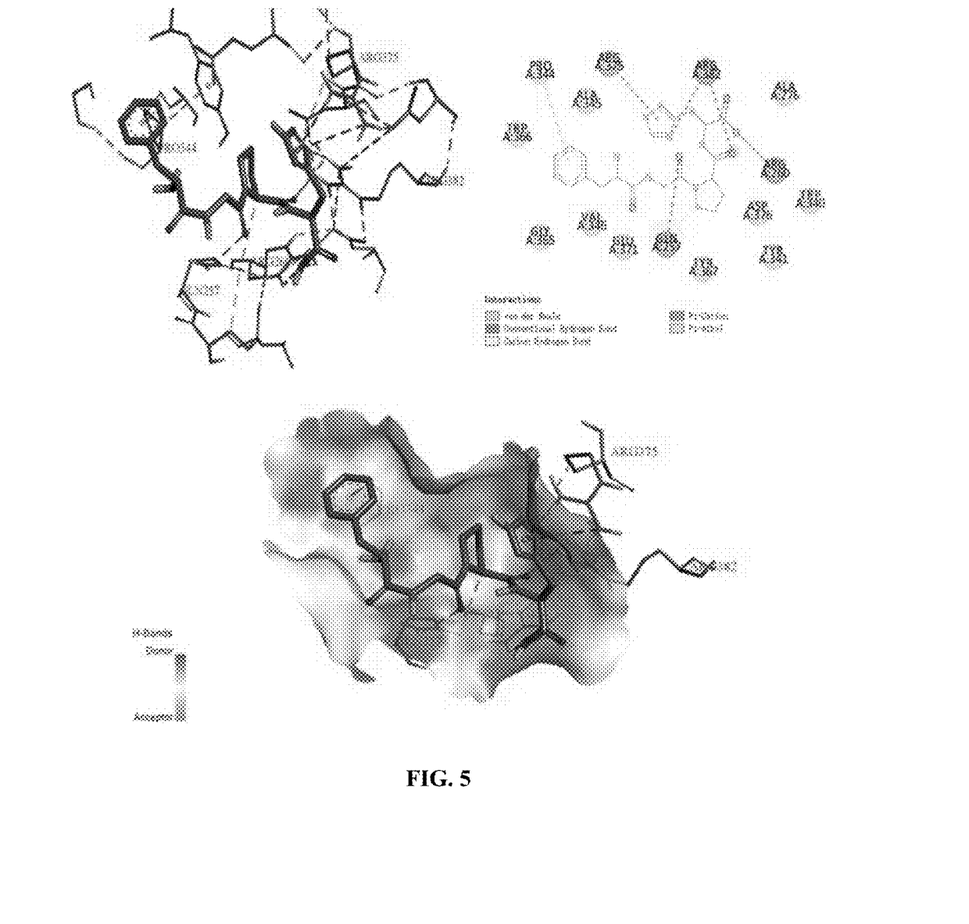
FIG. 5 is the interaction diagram of FGPH and iNOS.

The interaction between FGPH and iNOS is shown in FIG. 5. Gln257 of iNOS forms a hydrogen bond interaction with the carbonyl oxygen atom of Gly of FGPH, and a carbon-hydrogen bond with Pro. Arg260 forms a hydrogen bond interaction with the carboxyl group of His. Arg382 forms two hydrogen bonds interaction with the nitrogen atom of His and the carbonyl oxygen atom of Pro. Pro344 forms a 7-alkyl interaction with the benzene ring of Phe. Arg375 forms two cation-π interactions with the imidazole ring of His.

Example 3 Polypeptide Synthesis and Artificial Verification

The peptides were synthesized through solid-phase synthesis, entrusted to Nanjing Yuantai Biotechnology Co., Ltd. The purity is ≥95%, which meets the requirements of experiments related to activity detection.

1. Analysis of Anti-Inflammatory Activity of FGPH
1.1 Cell Viability

Figure 6:
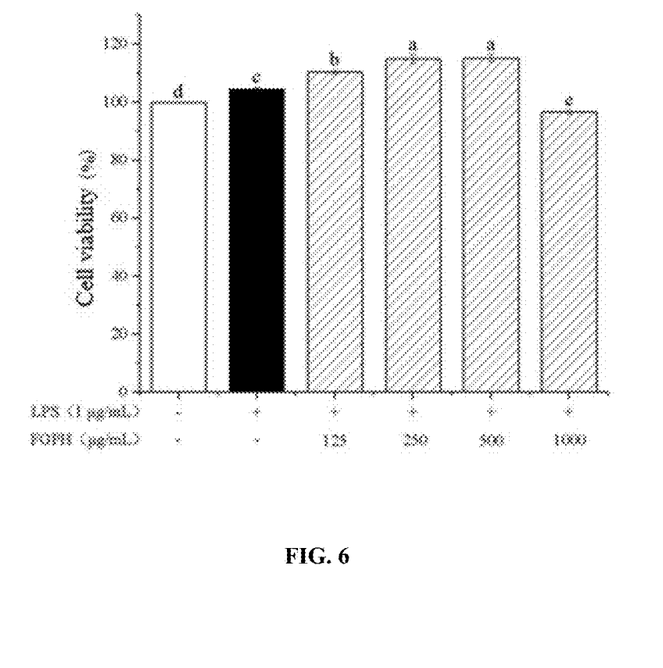
FIG. 6 illustrates the effect of FGPH on the cell viability.

The effect of FGPH of different concentrations on the cell viability were explored. As shown in FIG. 6, within the concentration range of 125 to 1000 μg/mL, the effect of FGPH on the cell viability of RAW264.7 cells induced by LPS showed a trend of first increasing and then decreasing as the peptide concentration increased. When the concentration of FGPH was 125, 250, and 500 μg/mL, the cell viability was higher than 109%, which promoted the cell proliferation. When the concentration of FGPH was 1000 μg/mL, the cell viability was lower than 97%, which inhibited the cell viability. Therefore, FGPH has a certain ability to promote the cell proliferation. When the concentration of FGPH was selected from 125 to 500 μg/mL, the effect on NO production amount and inflammatory factor secretion in RAW264.7 cells induced by LPS was further determined.

1.2 Anti-Inflammatory Activity of FGPH

The effect of FGPH with a concentration in the range of 125 to 500 μg/mL on the NO production amount and the secretion of inflammatory factors TNF-α, IL-1β, and IL-6 in RAW264.7 cells induced by LPS were explored.

Figure 7:
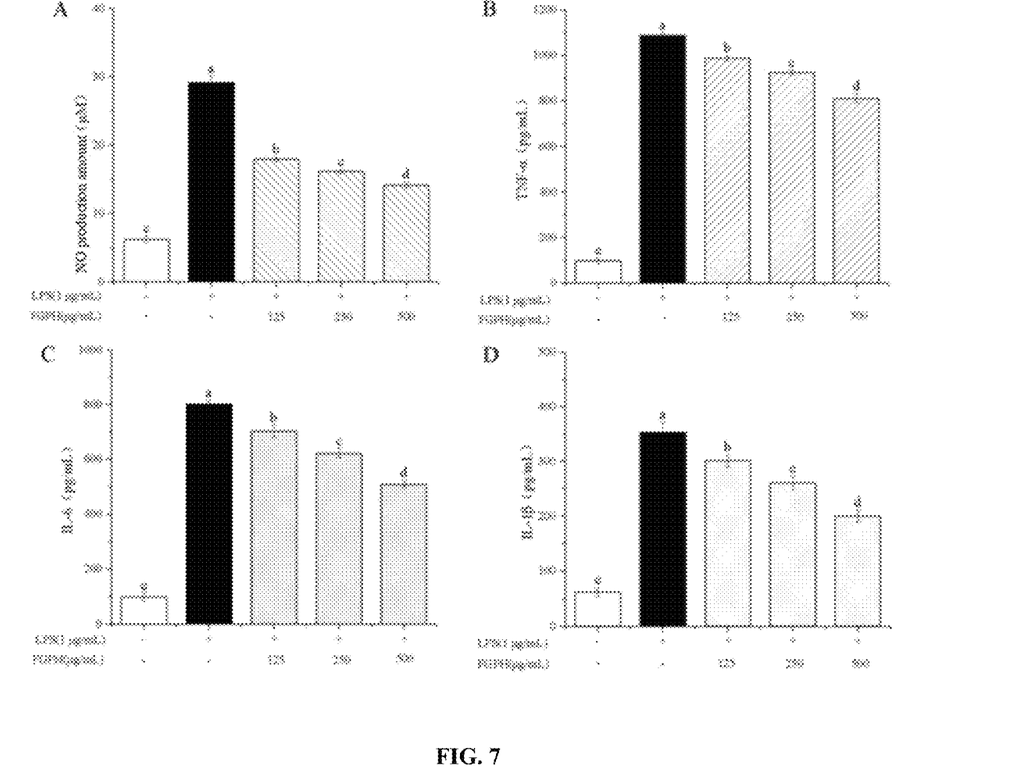
FIG. 7 illustrates the effects of different concentrations of FGPH on cellular NO (A), TNF-α (B), IL-6 (C), and IL-1β (D) secretion.

As shown in FIG. 7A, after being induced by LPS at a concentration of 1 μg/mL, the NO production amount of RAW264.7 cells increased significantly ($P<0.05$), which was approximately 4.94 times that of the blank group, indicating that the RAW264.7 macrophage inflammation model induced by LPS was successfully established. Compared with the LPS group, FGPH had a significant inhibitory effect on the NO production amount of RAW264.7 cells induced by LPS at the concentrations of 125, 250, and 500 μg/mL ($P<0.05$). Under the effects of these three concentrations of FGPH, the NO production amounts of the cells were 18.07±0.31, 16.23±0.31, and 13.82±0.31 μM, respectively. It can be seen that FGPH significantly inhibits the NO production amount in RAW264.7 cells induced by LPS in a concentration-dependent manner. As the concentration of FGPH increases, the inhibitory effect on the NO production amount in the cells becomes more obvious. When the concentration of FGPH was 500 μg/mL, the NO production amount was the lowest, and the NO production amount inhibition ratio was the highest, reaching 64.41±0.47%.

As shown in FIG. 7B, after being induced with LPS at a concentration of 1 μg/mL, the secretion of TNF-α in RAW264.7 cells increased significantly ($P<0.05$), which was approximately 11.03 times that of the blank group. FGPH at three concentrations all can significantly inhibit the secretion of TNF-α in the cells ($P<0.05$), showing concentration-dependent characteristics. The highest inhibition ratio was 28.07±2.10% at a concentration of 500 μg/mL FGPH.

As shown in FIG. 7C, after being induced with LPS at a concentration of 1 μg/mL, the amount of IL-6 secreted by cells increased significantly ($P<0.05$), which was approximately 8.05 times that of the blank group. Compared with the LPS group, FGPH had a significant inhibitory effect on the IL-6 secretion of macrophages induced by LPS at concentrations of 125, 250, and 500 μg/mL ($P<0.05$). FGPH significantly inhibited the IL-6 secretion of RAW264.7 cells induced by LPS in a concentration-dependent manner, and as the concentration of FGPH increases, the inhibitory effect on the IL-6 secretion of cells became better. When the concentration of FGPH was 500 μg/mL, reaching 41.72±1.83%.

As shown in FIG. 7D, after being induced with LPS at a concentration of 1 μg/mL, the secretion of IL-1β in cells significantly increased ($P<0.05$), which was approximately 5.68 times that of the blank group. Compared with the LPS group, FGPH had a significant inhibitory effect on the IL-1β secretion of LPS-induced cells at concentrations of 125, 250, and 50 μg/mL ($P<0.05$). FGPH significantly inhibited the IL-1β secretion of RAW264.7 cells induced by LPS in a concentration-dependent manner, and as the concentration of FGPH increases, the inhibitory effect on the IL-1β secretion of cells became better. When the concentration of FGPH was 500 μg/mL, reaching 52.43±2.29%.

2. Analysis of Antioxidant Activity of FGPH

The $EC_{50}$ value of antioxidant capacity of FGPH is shown in Table 6. FGPH has the ability to scavenge three free radicals: DPPH, ABTS and hydroxyl radicals, so it has a certain antioxidant activity.

TABLE 6

| Antioxidant capacity of FGPH | |
| --- | --- |
| Antioxidant activity | $EC_{50}$ value (mg/mL) |
| Scavenging DPPH free radical | 4.96 ± 0.05 |
| Scavenging ABTS free radical | 0.81 ± 0.01 |
| Scavenging hydroxyl radical | 2.01 ± 0.03 |

Example 4 Maillard Reaction of FGPH

1. Preparation Method

A certain amount of FGPH was weighed and prepared into a 20 mg/mL solution.

The dextran was added according to a peptide to dextran mass ratio of 1.5:1, mixed thoroughly, and reacted for 10 hours at a temperature of 80° C. and a pH value of 9.0. After the reaction was completed, cooling was performed to room temperature, the Maillard product of FGPH, FGPH-MRPs, was obtained.

Taking the production amount of Maillard intermediate products represented by the absorbance value at 294 nm and the browning degree represented by the absorbance value at 420 nm as indicators, the absorbance value of the above-mentioned Maillard product FGPH-MRPs at 294 nm was 0.736±0.010, and the absorbance value at 420 nm was 0.696±0.010.

2. Determination of Physical and Chemical Properties

2.1 Fourier Transform Infrared (FTIR) Analysis

Figure 8:
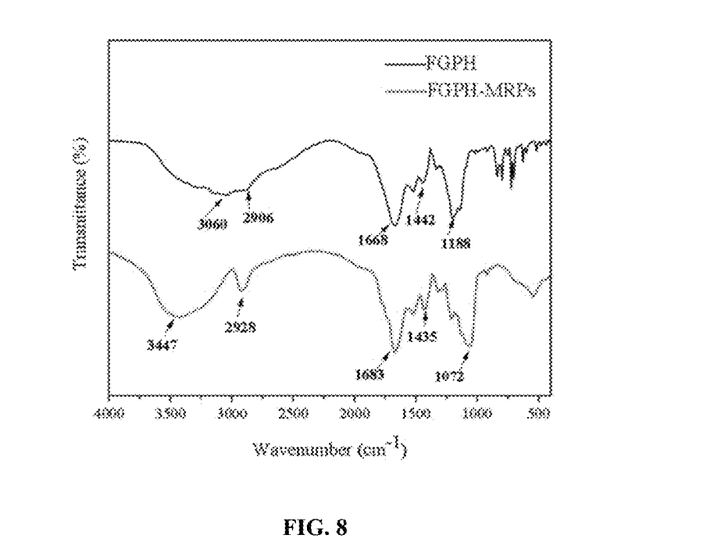
FIG. 8 is the infrared spectrum analysis diagram of FGPH and FGPH-MRPs.

The Fourier transform infrared spectra of FGPH and FGPH-MRPs are shown in FIG. 8. Fourier transform infrared spectroscopy is often used to study the interactions between protein and carbohydrate and to characterize changes in protein structure. The protein has multiple characteristic absorption peaks in the infrared spectrum, in which the amide I band, amide II band, and amide III band has absorption at 1700 to 1600 $cm^{-1}$, 1600 to 1500 $cm^{-1}$, and 1450 to 1240 $cm^{-1}$, respectively. Compared with proteins, peptides are small molecular substances derived from proteins, in which most of the secondary structures of proteins disappear, and the absorption peak in the amide II band is not obvious. After the protein/peptide undergoes Maillard reaction, it shows two typical characteristics in the infrared spectrum. One is due to the stretching vibration of the free hydroxyl group, a broad peak appears in the infrared spectrum in the range of 3500 to 3000 $cm^{-1}$; the other is due to the stretching vibration of the C—O bond, an obvious absorption peak appears in the range of 1260 to 1000 $cm^{-1}$. As shown in FIG. 8, the absorption of FGPH-MRPs at 3500 to 3000 $cm^{-1}$ and 1260 to 1000 $cm^{-1}$ is higher than that of FGPH, indicating that the Maillard reaction has occurred.

The peak of FGPH in the amide I band is located at 1668 $cm^{-1}$, and the peak of FGPH-MRPs in the amide I band is blue-shifted to 1683 $cm^{-1}$. This is mainly due to the reaction of —NH with —C=O, and the carbonyl electron cloud density is reduced, causing the peak position to be blue-shifted. FGPH-MRPs has a more obvious absorption peak than FGPH at the amide III band at 1435 $cm^{-1}$. This is because the C—H plane in the structure of the aromatic amino acid phenylalanine is bent outward. The above also proves the occurrence of the Maillard reaction.

2.2 Scanning Electron Microscope (SEM) Analysis

Figure 9:
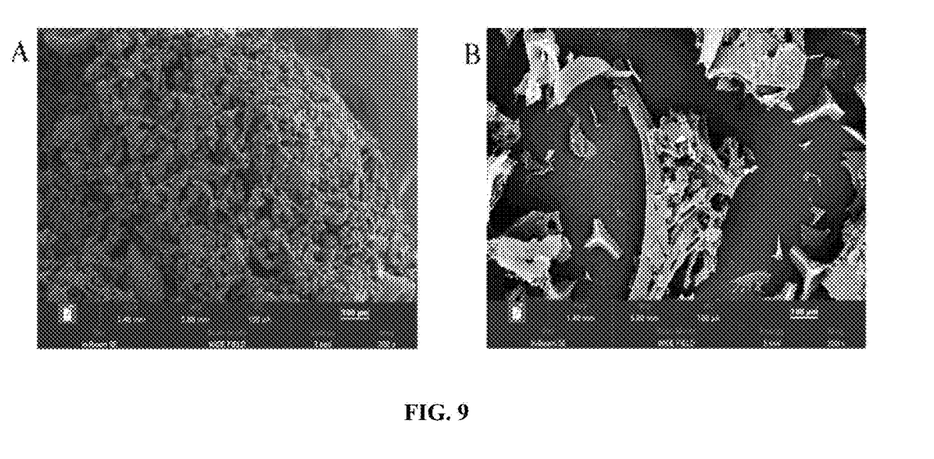
FIG. 9 is the scanning electron microscope images of FGPH (A) and FGPH-MRPs (B).

FGPH and FGPH-MRPs were placed under a scanning electron microscope and magnified at the same magnification. The SEM image of FGPH was shown in FIG. 9A, and the SEM image of FGPH-MRPs was shown in FIG. 9B. The micromorphology of FGPH changed significantly after the Maillard reaction, and FGPH-MRPs showed an irregular flake structure with pores.

2.3 Effect on RAW264.7 Cell Viability

Figure 10:
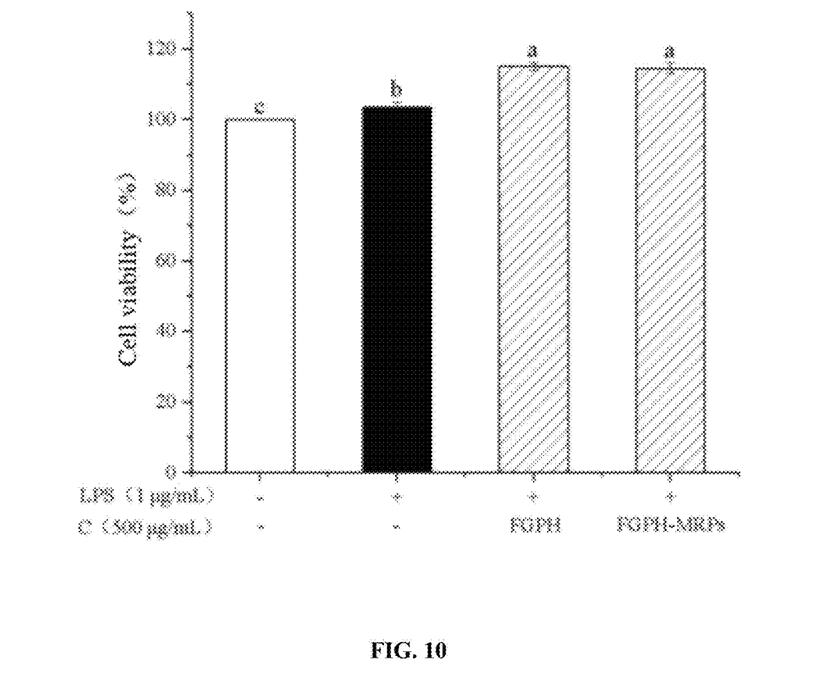
FIG. 10 illustrates the effects of FGPH and FGPH-MRPs on the cell viability.

The effects of FGPH and FGPH-MRPs on cell viability at 500 μg/mL were explored. As shown in FIG. 10, the cell viabilities of RAW264.7 induced by LPS under the action of two samples with a concentration of 500 μg/mL were both above 114%, indicating a certain cell proliferation ability. The cell viabilities of the two samples have no significant differences ($P>0.05$).

2.4 Effect on NO Production Amount in RAW264.7 Cells

Figure 11:
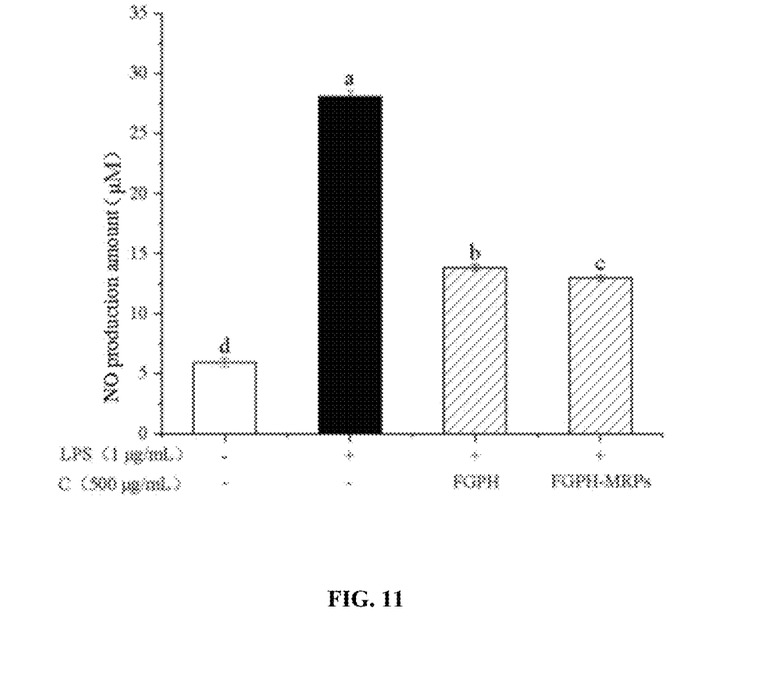
FIG. 11 illustrates the effects of FGPH and FGPH-MRPs on the cellular NO production amount.

As shown in FIG. 11, after being induced by LPS at a concentration of 1 μg/mL, the NO production amount of RAW264.7 cells increased significantly ($P<0.05$), which was approximately 4.94 times that of the blank group, indicating that the RAW264.7 macrophage inflammation model induced by LPS was successfully established. Compared with the LPS group, both FGPH and FGPH-MRPs significantly inhibited the NO production amount of RAW264.7 cells induced by LPS at a concentration of 500 μg/mL ($P<0.05$). After Maillard reaction, the inhibition ratio of NO production amount increased from 64.41±0.47% to 68.16±0.48%.

2.5 Effect of Maillard Reaction on Antioxidant Activity

The antioxidant capabilities of FGPH and FGPH-MRPs were shown in Table 7. After the Maillard reaction of FGPH, the $EC_{50}$ value of DPPH, ABTS and hydroxyl radical scavenging rate decreased ($P<0.05$), indicating that the Maillard reaction contributes to the improvement of the antioxidant activity of FGPH.

TABLE 7

Antioxidant capacity of FGPH and FGPH-MRPs

| Antioxidant activity | $EC_{50}$ value (mg/mL) | |
| --- | --- | --- |
|  | FGPH | FGPH-MRPs |
| Scavenging DPPH free radical | 4.96 ± 0.05[a] | 4.07 ± 0.03 |
| Scavenging ABTS free radical | 0.81 ± 0.01[a] | 0.61 ± 0.01[b] |
| Scavenging hydroxyl radical | 2.01 ± 0.03[a] | 1.56 ± 0.02[b] |

2.6 Exploring the Flavor Changes of FGPH Before and After Maillard Reaction Using Sensory Evaluation, Electronic Tongue, and Electronic Nose

The flavors of FGPH and FGPH-MRPs before and after the Maillard reaction were tested through sensory evaluation, electronic tongue and electronic nose evaluation. The taste of FGPH-MRPs was significantly better than that of FGPH, and the bitterness, astringency, and salty taste were masked to a certain extent. The overall receptivity of FGPH-MRPs was higher than that of FGPH, and the Maillard characteristic mellow taste was obtained, and the smell was significantly changed. The electronic tongue and electronic nose can clearly distinguish FGPH from FGPH-MRPs.

2.6.1 Sensory Evaluation

Figure 12:
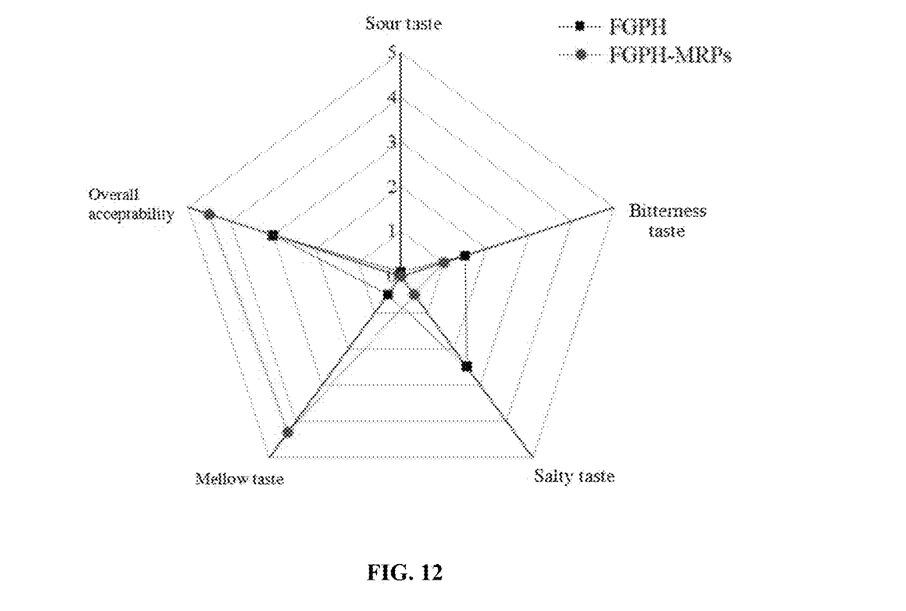
FIG. 12 is the radar chart of sensory evaluation of FGPH and FGPH-MRPs.

The sensory evaluation occupies an important position in the study of food taste characteristics. As shown in FIG. 12, the two samples have a large difference in sensory evaluation scores. In the bitterness, astringency, and salty taste scores, FGPH-MRPs is lower than FGPH. The Maillard reaction helps to mask the bad taste. In the mellow taste score and the overall acceptability score, FGPH-MRPs is higher than FGPH. The taste of the sample is significantly improved after the Maillard reaction, and the Maillard characteristic mellow taste is clearly reflected.

2.6.2 Electronic Tongue Evaluation

Figure 13:
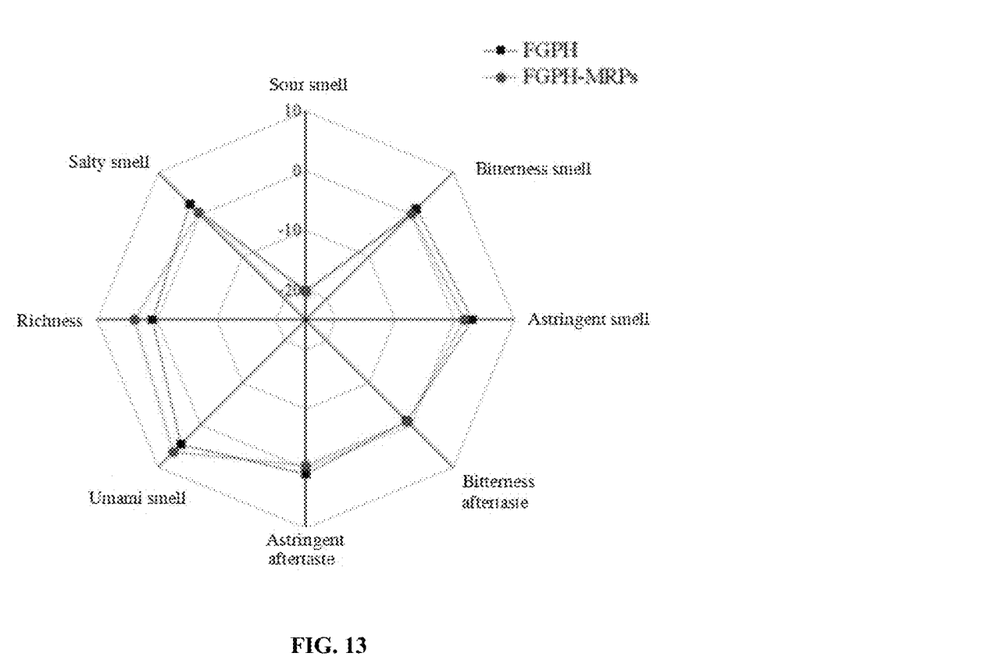
FIG. 13 is the electronic tongue taste index radar chart of FGPH and FGPH-MRPs.

The electronic tongue was used to compare the taste values of FGPH and FGPH-MRPs and create a taste radar chart. No sour or bitter aftertaste was detected in the two samples. As shown in FIG. 13, the Maillard product FGPH-MRPs has lower bitterness, astringency, and salty than FGPH, respectively, indicating that the Maillard reaction can mask unpleasant tastes to a certain extent. FGPH itself has a certain umami taste and richness. After the Maillard reaction, the umami taste is further improved, indicating that the Maillard reaction helps to highlight the characteristic taste of the peptide.

2.6.3 Electronic Nose Evaluation

Figure 14:
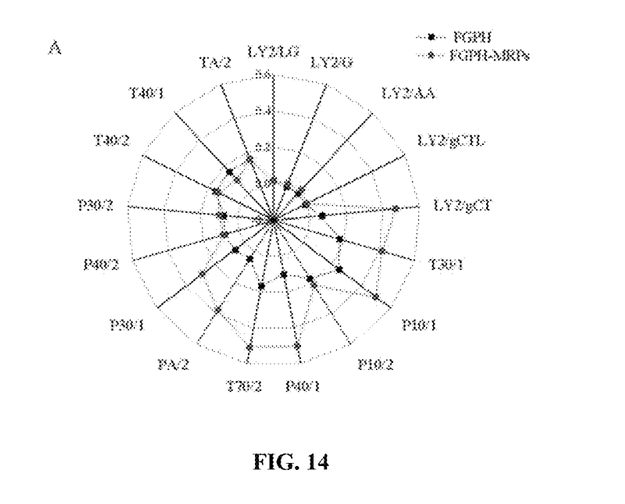
FIG. 14 is the electronic nose odor indicator radar chart of FGPH and FGPH-MRPs.

The odor radar diagram of FGPH and FGPH-MRPs in the electronic nose sensor was shown in FIG. 14. The odor changed significantly before and after the Maillard reaction. The response values of FGPH-MRPs on LY2/gCT, T30/1, P10/1, P40/1, T70/2, PA/2, and P30/1 sensors were significantly higher than that of FGPH. The free amino group of the peptide FGPH in the present application was located on phenylalanine. The electronic nose response value of the volatile flavor substances of the phenylalanine Maillard product was high, and the characteristic Maillard odor was obtained.

After the Maillard reaction, the overall taste of FGPH was improved and the smell was more obvious.

The above embodiments are only several exemplary embodiments of the present application, and their descriptions are relatively specific and detailed, which should not be construed as limiting the scope of the present application. It should be noted that, for those of ordinary skill in the art, several modifications, combinations and improvements can be made to each of the above embodiments without departing from the concept of the present application, and these all fall within the protection scope of the present application. Therefore, the protection scope of the present application should be determined by the claims.

```
                         SEQUENCE LISTING

Sequence total quantity: 9
SEQ ID NO: 1            moltype = AA  length = 4
FEATURE                 Location/Qualifiers
source                  1..4
                        mol_type = protein
                        organism = unidentified
SEQUENCE: 1
FGPH                                                                       4

SEQ ID NO: 2            moltype = AA  length = 7
FEATURE                 Location/Qualifiers
source                  1..7
                        mol_type = protein
                        organism = unidentified
SEQUENCE: 2
WNIPIGT                                                                    7

SEQ ID NO: 3            moltype = AA  length = 9
FEATURE                 Location/Qualifiers
source                  1..9
                        mol_type = protein
                        organism = unidentified
SEQUENCE: 3
AGWNIPIGT                                                                  9

SEQ ID NO: 4            moltype = AA  length = 4
FEATURE                 Location/Qualifiers
source                  1..4
                        mol_type = protein
                        organism = unidentified
SEQUENCE: 4
WNIP                                                                       4

SEQ ID NO: 5            moltype = AA  length = 9
FEATURE                 Location/Qualifiers
source                  1..9
                        mol_type = protein
                        organism = unidentified
SEQUENCE: 5
AGWNIPIGT                                                                  9

SEQ ID NO: 6            moltype = AA  length = 7
FEATURE                 Location/Qualifiers
source                  1..7
                        mol_type = protein
                        organism = unidentified
SEQUENCE: 6
RADHPFL                                                                    7

SEQ ID NO: 7            moltype = AA  length = 8
FEATURE                 Location/Qualifiers
source                  1..8
                        mol_type = protein
                        organism = unidentified
SEQUENCE: 7
FPFEVFGK                                                                   8
```

-continued

```
SEQ ID NO: 8           moltype = AA  length = 7
FEATURE                Location/Qualifiers
source                 1..7
                       mol_type = protein
                       organism = unidentified
SEQUENCE: 8
FGRCVSP                                                                  7

SEQ ID NO: 9           moltype = AA  length = 8
FEATURE                Location/Qualifiers
source                 1..8
                       mol_type = protein
                       organism = unidentified
SEQUENCE: 9
FFGRCVSP                                                                 8
```

What is claimed is:

1. An anti-inflammatory active peptide that is the amino acid sequence Phe-Gly-Pro-His (SEQ ID NO: 1).

2. An anti-inflammatory drug or food comprising the anti-inflammatory active peptide according to claim 1.

3. A Maillard reaction product of a peptide that is the amino acid sequence Phe-Gly-Pro-His (SEQ ID NO:1), made by adding a dextran to an aqueous solution comprising the peptide according to a peptide to dextran mass ratio of 1.5:1, mixing thoroughly, reacting at 80° C. and pH 9.0 for 10 hours, and cooling to room temperature after the reacting is completed, to obtain the Maillard reaction product.

\* \* \* \* \*